(12) United States Patent
Frey et al.

(10) Patent No.: US 8,238,522 B2
(45) Date of Patent: Aug. 7, 2012

(54) FILTER CHANGING ASSEMBLY FOR FILTERING A RADIATION BEAM

(75) Inventors: Christof Frey, Hunzenschwill (CH); Reto Filiberti, Steinhausen (CH); Juerg Zinniker, Aarau (CH)

(73) Assignee: Varian Medical Systems International AG, Zug (CH)

( * ) Notice: Subject to any disclaimer, the term of this patent is extended or adjusted under 35 U.S.C. 154(b) by 180 days.

(21) Appl. No.: 12/758,239

(22) Filed: Apr. 12, 2010

(65) Prior Publication Data

US 2011/0249787 A1   Oct. 13, 2011

(51) Int. Cl.
*G21K 3/00*     (2006.01)

(52) U.S. Cl. .................................. 378/158; 378/156

(58) Field of Classification Search .................. 378/145, 378/156–161
See application file for complete search history.

(56) References Cited

U.S. PATENT DOCUMENTS

2002/0186817 A1* 12/2002 Schukalski et al. ........... 378/156
2007/0025520 A1*  2/2007 Thandiackal et al. ........ 378/157

* cited by examiner

*Primary Examiner* — Hoon Song

(57) ABSTRACT

A filter changing assembly that can be used in, for example, a radiology system includes shape filters that can used to shape a radiation beam and that can be moved back-and-forth, for example. The filter changing assembly also includes beam hardening filters that can be used to change the energy spectrum of the radiation beam, and that also can be moved back-and-forth, for example. The filter changing assembly includes a control system that can be used to select at least one of the filters and automatically move the selected filter from one position to another position.

15 Claims, 6 Drawing Sheets

FILTER CHANGING ASSEMBLY FOR FILTERING A RADIATION BEAM

BACKGROUND

Computed tomography (CT) is an imaging technique that is widely used in the medical field. In general, an x-ray source and a detector are positioned on opposite sides of a patient. The x-ray source generates and directs an x-ray beam towards the patient, while the detector measures the x-ray absorption along different transmission paths. By taking many readings from multiple angles around the patient, relatively large amounts of data can be accumulated. That data can then be analyzed and processed to construct a three-dimensional representation of the patient's insides.

While performing CT, a filter is generally placed between the patient and the x-ray source in order to, for example, reduce the intensity of the x-ray beam or shape the x-ray beam, thereby reducing the radiation dose experienced by the patient. One class of filter (e.g., beam hardening filters) may be used to change the beam's energy spectrum, and another class of filter (e.g., shape filters) may be used to change the beam's shape. Within each class of filter, there may be a number of different filters—that is, there may be a number of different beam hardening filters, and a number of different shape filters. Different filters are selected and used depending on, for example, the types of procedures to be performed.

In one conventional implementation, a filter is selected and manually placed in a fixed position inside the beam path. To change the filter to a different one, an operator must enter the treatment room, manually remove the installed filter, and insert the new filter. Consequently, the process of setting up a different filter, including alignment and perhaps calibration, can take a relatively long time. From the patient's perspective, the wait may be both inconvenient and uncomfortable.

In another conventional implementation, a motor is used to move a filter into a filtering position in the beam path. However, if a different filter is to be used, an operator must still enter the treatment room and manually replace that filter with another in a manner similar to that just described.

There are other types of conventional implementations in use, but in general those implementations share the problems described above.

SUMMARY

According to embodiments of the invention, a filter changing assembly that can be used in, for example, a radiology system includes shape filters that can used to shape a radiation beam and that can be moved back-and-forth, for example. The filter changing assembly also includes beam hardening filters that can be used to change the energy spectrum of the radiation beam, and that also can be moved back-and-forth, for example. The filter changing assembly includes a control system that can be used to select at least one of the filters and automatically move the selected filter from one position to another position.

In one embodiment, the filter changing assembly includes shape filters that can be moved between a first filtering position between a radiation source and a target and a first storage position that is outside of the radiation beam's path. The filter changing assembly also includes beam hardening filters that also can be moved between a second filtering position between the radiation source and the target and a second storage position that is outside of the radiation beam's path. The filter changing assembly includes a control system that can be used to select at least one of the filters and automatically move the selected filter from its storage position to its filtering position.

The filter changing assembly can be used in a radiology system (e.g., a radiographic imaging system such as a computed tomography system) to scan the insides of an object (e.g., a piece of luggage) or a subject (e.g., a human patient). For medical procedures, the filter changing assembly can be used during diagnosis and/or treatment.

There are a number of advantages associated with the disclosed filter changing assembly. For example, filters can be changed remotely and automatically so that the operator does not need to enter the treatment room, which speeds up the setup process. The position of each filter can be repeated, which also speeds up the setup process—for example, the radiology system can be calibrated with a certain filter in place in a particular position, and then that filter can be precisely returned to that position with a patient in place. Also, different combinations of filters can be selected and readily moved in and out of position. Furthermore, mechanical features of the filter changing assembly allow the position of each filter to be fine-tuned. Other mechanical features of the assembly prevent filters from being inadvertently dropped or from falling on a patient. Errors are reduced or even eliminated, because the possibility of installing an incorrect filter or combination of filters is reduced if not altogether eliminated.

These and other objects and advantages of the various embodiments of the invention will be recognized by those of ordinary skill in the art after reading the following detailed description of the embodiments that are illustrated in the various drawing figures.

BRIEF DESCRIPTION OF THE DRAWINGS

The accompanying drawings, which are incorporated in and form a part of this specification, illustrate embodiments of the invention and, together with the description, serve to explain the principles of the invention. Unless noted otherwise, the drawings are not to scale.

DETAILED DESCRIPTION

Figure 1:
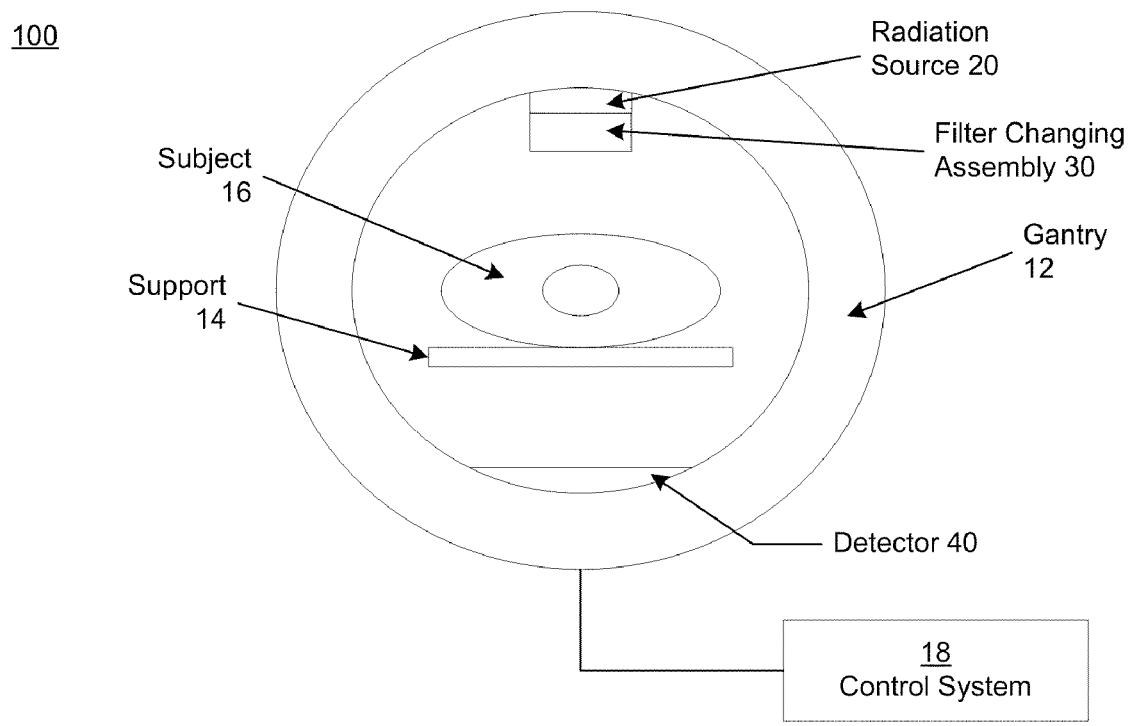
FIG. 1 illustrates elements of a radiology system in an embodiment according to the invention.

Reference will now be made in detail to embodiments of the present invention, examples of which are illustrated in the accompanying drawings. While the invention will be described in conjunction with these embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of embodiments of the present invention, numerous specific details are set forth in order to provide a thorough understanding of the present invention. However, it will be recognized by one of ordinary skill in the art that the present invention may be practiced without these specific details. In other instances, well-known methods, procedures, components, and circuits have not been described in detail as not to unnecessarily obscure aspects of the embodiments of the present invention.

Some portions of the detailed descriptions, which follow, are presented in terms of procedures, steps, logic blocks, processing, and other symbolic representations of operations on data bits within a computer memory. These descriptions and representations are the means used by those skilled in the data processing arts to most effectively convey the substance of their work to others skilled in the art. A procedure, computer-executed step, logic block, process, etc., is here, and generally, conceived to be a self-consistent sequence of steps or instructions leading to a desired result. The steps are those requiring physical manipulations of physical quantities. Usually, though not necessarily, these quantities take the form of electrical or magnetic signals capable of being stored, transferred, combined, compared, and otherwise manipulated in a computer system. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present invention, discussions utilizing terms such as "receiving," "selecting," "causing," "identifying," "generating" or the like, refer to the actions and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Some embodiments described herein may be discussed in the general context of computer-executable instructions or components residing on some form of computer-usable medium, such as program modules, executed by one or more computers or other devices. Generally, program modules include routines, programs, objects, data structures, etc., that perform particular tasks or implement particular abstract data types. The functionality of the program modules may be combined or distributed as desired in various embodiments.

By way of example, and not limitation, computer-usable media may comprise computer storage media and communication media. Computer storage media includes volatile and nonvolatile, removable and non-removable media implemented in any method or technology for storage of information such as computer-readable instructions, data structures, program modules or other data. Computer storage media includes, but is not limited to, random access memory (RAM), read only memory (ROM), electrically erasable programmable ROM (EEPROM), flash memory or other memory technology, compact disk ROM (CD-ROM), digital versatile disks (DVDs) or other optical storage, magnetic cassettes, magnetic tape, magnetic disk storage or other magnetic storage devices, or any other medium that can be used to store the desired information.

Communication media can embody computer-readable instructions, data structures, program modules or other data and includes any information delivery media. By way of example, and not limitation, communication media includes wired media such as a wired network or direct-wired connection, and wireless media such as acoustic, radio frequency (RF), infrared and other wireless media. Combinations of any of the above should also be included within the scope of computer-readable media.

FIG. 1 illustrates elements of a radiology system 100 in an embodiment according to the invention. In one embodiment, the system 100 is a computed tomography (CT) system, specifically a cone beam CT (CBCT) system. The system 100 can be used for medical applications including diagnosis and treatment. However, the system 100 is not so limited and can be used to scan objects other than human subjects, such as luggage, for example.

In the example of FIG. 1, the system 100 includes a support 14 (e.g., a flat surface such as a bed or table) for an object or subject 16 to be scanned (imaged) and/or treated. In operation, the support 14 and subject 16 are situated within an opening in a gantry 12. The system 100 also includes a radiation source 20 (e.g., an x-ray tube) that is attached to the gantry 12 and that projects a beam of radiation towards a target (e.g., to and through the subject 16, and to the detector 40). The radiation source 20 can generate beams at different energy levels (measured in keV).

The detector 40 includes a number of sensor elements that can sense the intensity (e.g., amount and/or energy level) of the radiation that passes through the subject 16. The gantry 12 can rotate about the subject 16, and can move back and forth along the length of the subject 16 (or the position of the subject can be moved relative to the position of the gantry). The control system 18 can be used to control operation of the gantry 12, and can also be used to control the radiation source 20 and the filter changing assembly 30.

The filter changing assembly 30 is positioned between the radiation source 20 and the detector 40. A blade (jaw) assembly (not shown), which contains some number of motorized and position-controlled blades (e.g., four blades), can be located between the radiation source 20 and the filter changer assembly 30, in order to narrow the beam so that no elements external to the active surface of the detector 40 are irradiated. The blades can be remotely controlled and respectively pre-programmed to any intermediate position either symmetrically or asymmetrically.

The filter changing assembly 30 includes multiple (e.g., at least two) filter decks or sliders. In one embodiment, the filter changing assembly 30 includes a beam hardening (or foil) filter slider and a shape filter slider. The beam hardening filter slider includes multiple beam hardening filters, and the shape filter slider likewise includes multiple shape filters. Additional information is provided in conjunction with the discussion of FIGS. 2, 3, and 4, below.

Continuing with reference to FIG. 1, a beam hardening (foil) filter is used to change the energy spectrum of the radiation beam. For example, a beam hardening filter can be used to filter out lower energy x-rays, changing the x-ray spectrum to a "harder" beam with a larger proportion of higher energy x-rays. The lower energy x-rays tend to get absorbed by the subject 16 and thus do not reach the detector 40 (and hence do not contribute to the resultant image), and so only increase the dose to the subject. By hardening the beam, the dose to the subject 16 can be reduced.

The areas of the detector 40 that are not covered by the subject 16 get the direct beam (the part of the beam not attenuated by the subject), which will saturate those areas much sooner than the areas covered by the subject. Also, in a human subject, for example, the beam will have to penetrate through less tissue at the edges of the subject than it will toward the center of the subject. In that case, the beam can be less intense toward the edges of the subject 16; if the intensity is too high, unwanted scatter can increase in those areas. A shape filter (e.g., a bow-tie filter) can be used to better fit the x-ray dose distribution to the subject 16 in order to reduce (minimize) the dose to that subject, to improve scatter behavior, and to improve the dynamic range of the detector 40. Also, because the radiation source 20 (x-ray tubes, for example) may not have a totally flat distribution of dose over the whole radiation field, a shape filter can be used to correct the field to make it flatter (more homogeneous).

In general, the filter changing assembly 30 can be used to provide different combinations of filters depending on the type of procedure to be performed or to modulate the radiation beam in different ways. For example, a particular beam hardening filter and a particular shape filter can each be selected and used together (in combination) to filter the radiation beam in a particular way, each filter hardening or shaping the beam in its own way, as described above.

Also, the filter changing assembly 30 has the capability to automatically select a filter from one or both of the aforementioned filter sliders and automatically move the selected filter (s) into a respective position inside, or substantially inside, the beam's path. In other words, as will be seen from the discussion below, the filters are stored in a position that is entirely outside of, or at least partially outside of, the path of the radiation beam; that position may be referred to herein as the storage position. Also, selected filters are automatically moved from their respective storage positions into a position that is, at least in part or entirely, inside the beam's path between the radiation source 20 and the subject 16; the latter position may be referred to herein as the filtering position. Generally speaking, the filtering position refers to the position of a filter that allows that filter to filter the radiation beam to the extent required by a selected radiation procedure (e.g., scan, imaging, treatment), and the storage position refers to the position of the filter when it is not in the filtering position. A filter can also be placed in an intermediate position between the extreme filtering position and the extreme storage position.

In one embodiment, the filters are selected and inserted depending on a selected radiation procedure. The control system 18 is capable of storing one or more positions for each filter to accommodate different beam profiles, different procedures, and different types of targets (e.g., different body shapes and sizes). For example, if an operator selects a pelvic CBCT scan, then the control system 18 automatically selects a beam hardening filter and a shape filter that were defined in advance for that type of scan, and then automatically causes those filters to be moved into a precise filtering position also defined in advance for that type of scan. Errors are reduced or even eliminated, because the possibility of installing an incorrect filter or combination of filters is reduced if not altogether eliminated.

Figure 2:
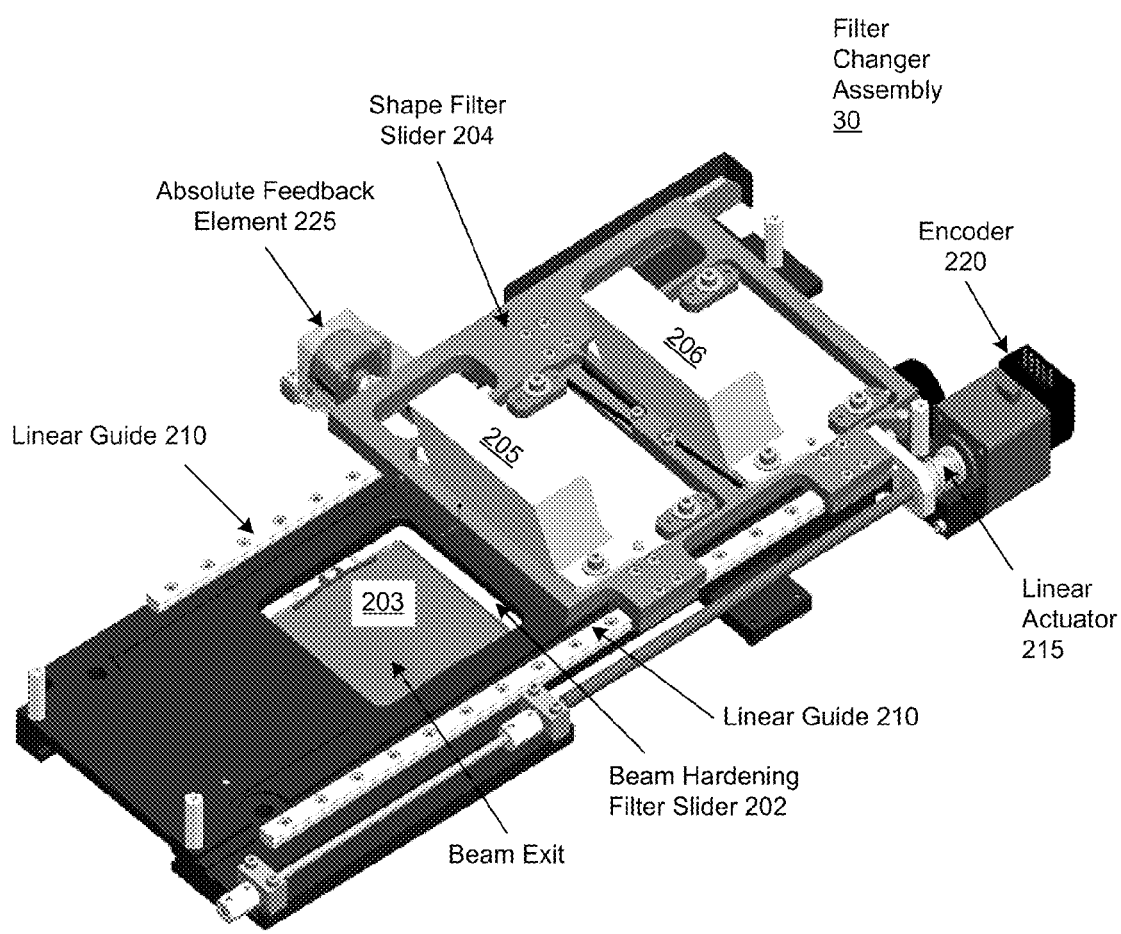
FIG. 2 illustrates an embodiment of a filter changing assembly according to the invention.

FIG. 2 illustrates an embodiment of a filter changing assembly 30 according to the invention. The bottom of the filter changing assembly 30 is shown. In other words, considering the orientation of the assembly in FIG. 2, a radiation beam would exit out of the page.

In one embodiment, the filter changing assembly 30 includes a beam hardening filter slider (or deck) 202 and a shape filter slider (or deck) 204. In such an embodiment, the beam hardening filter slider 202 includes multiple filters (not shown), and the shape filter slider includes two shape filters 205 and 206. In the example of FIG. 2, a beam hardening filter 203 is situated in a filtering position over the beam exit, while the shape filters 205 and 206 are situated in their storage positions. Either of the shape filters 205 or 206 can be automatically moved to a position over the beam exit by means of, for example, a motor and spindle (e.g., the linear actuator 215). More specifically, in one embodiment, the shape filter slider 204 is moved along the linear guides 210 until one or the other of the shape filters 205 and 206 is positioned over the beam exit.

Any of the positions in the slider 202 and the slider 204 can contain a "null" filter. Also, a filter in place in either of the sliders can be removed and replaced with a different filter. For example, a shape filter in the slider 204 can be removed and replaced with a different shape filter. Alternatively, a shape filter in the slider 204 can be removed and the position left empty—the unoccupied position is thus a null filter.

In one embodiment, an encoder 220 and an absolute feedback element (resolver) 225 are used to measure and monitor the position of the shape filter slider 204. The linear actuator 215 can move the filters by relatively small (precise) amounts, and the encoder 220 can likewise accurately measure the positions of the filters, so that the positions of the filters can be fine-tuned as needed. The absolute feedback element 225 can be used for initial calibration and as a diverse, redundant feedback of the slider position. The encoder 220 and the absolute feedback element 225 may be referred to generally as position detectors. Fine tuning of the filter position can be performed remotely from outside the treatment room and during radiation exposure.

The mechanical features of the filter changing assembly 30—specifically, the linear guides 210 and the encoder 220—ensure that the selected shape filter 205 or 206 is precisely located relative to the radiation beam and the beam exit. Similar mechanical features (not shown) ensure that the selected beam hardening filter 203 also is properly aligned with the beam exit. The precise nature of these mechanical features allows the filters to be positioned in virtually the same spot time-after-time.

This repeatability is advantageous, particularly for use of the beam shaping filter. For example, the system 100 (FIG. 1) can first be calibrated with filters in place but without a subject 16 to be scanned (e.g., with the patient not present). For instance, the offset gain correction can be calculated with the selected filters in a filtering position but without a subject 16. Subsequently, with the subject 16 now present, the selected filters can be returned to the filtering position and the scan can be performed. The offset gain correction can be subtracted from the raw image data collected by the detector 40, in order to derive the data that represents only the scanned subject. In other words, effects introduced by, for example, the support 14 are subtracted from the raw data. Thus, repeatability can improve the quality of the image data. Furthermore, repeatability decreases setup time, especially from the perspective of a human patient. In other words, a human patient need not be present while the system 100 is set up and calibrated and therefore, from the patient's perspective, the amount of time needed for the scan, imaging, or treatment process is greatly reduced.

In addition to the advantages just described, there are a number of other advantages associated with the filter changing assembly 30. For example, filters can be changed remotely and automatically so that an operator does not need to enter the treatment room, which further speeds up the setup process. Also, different combinations of filters can be selected and readily moved in and out of position.

The shape and beam hardening filters are each securely mounted within the filter changing assembly 30. The filter changing assembly 30 itself may be enclosed within a housing. Accordingly, filters are prevented from being inadvertently dropped or from falling on the subject 16.

As an alternative to the sliders 202 and 204 discussed above, a carousel type of structure can be used, in which the filters are rotated to and from their respective storage and filtering positions or any intermediate position.

Figure 3:
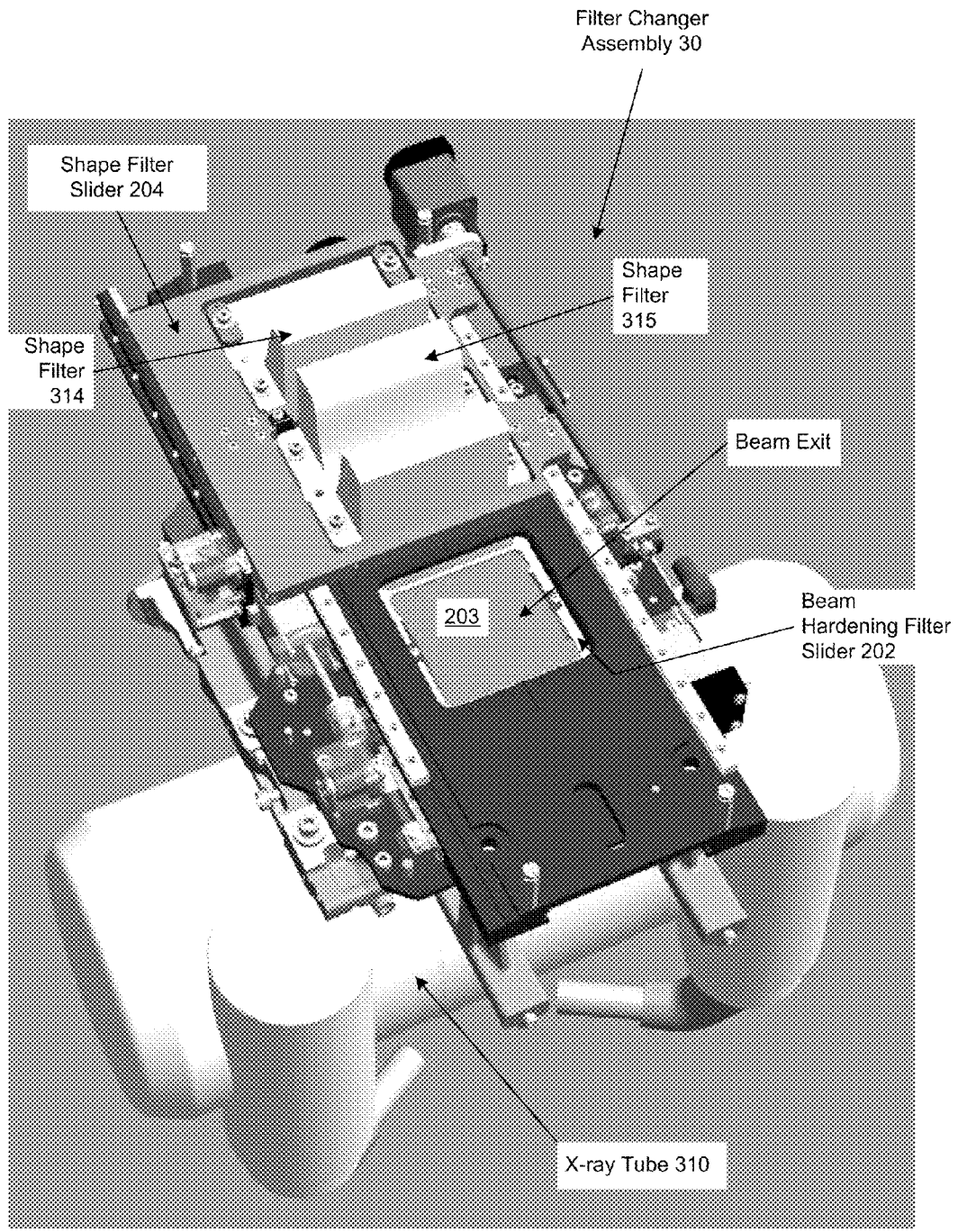
FIGS. 3 and 4 illustrate an embodiment of a filter changing assembly and an x-ray tube according to the invention.
Figure 4:
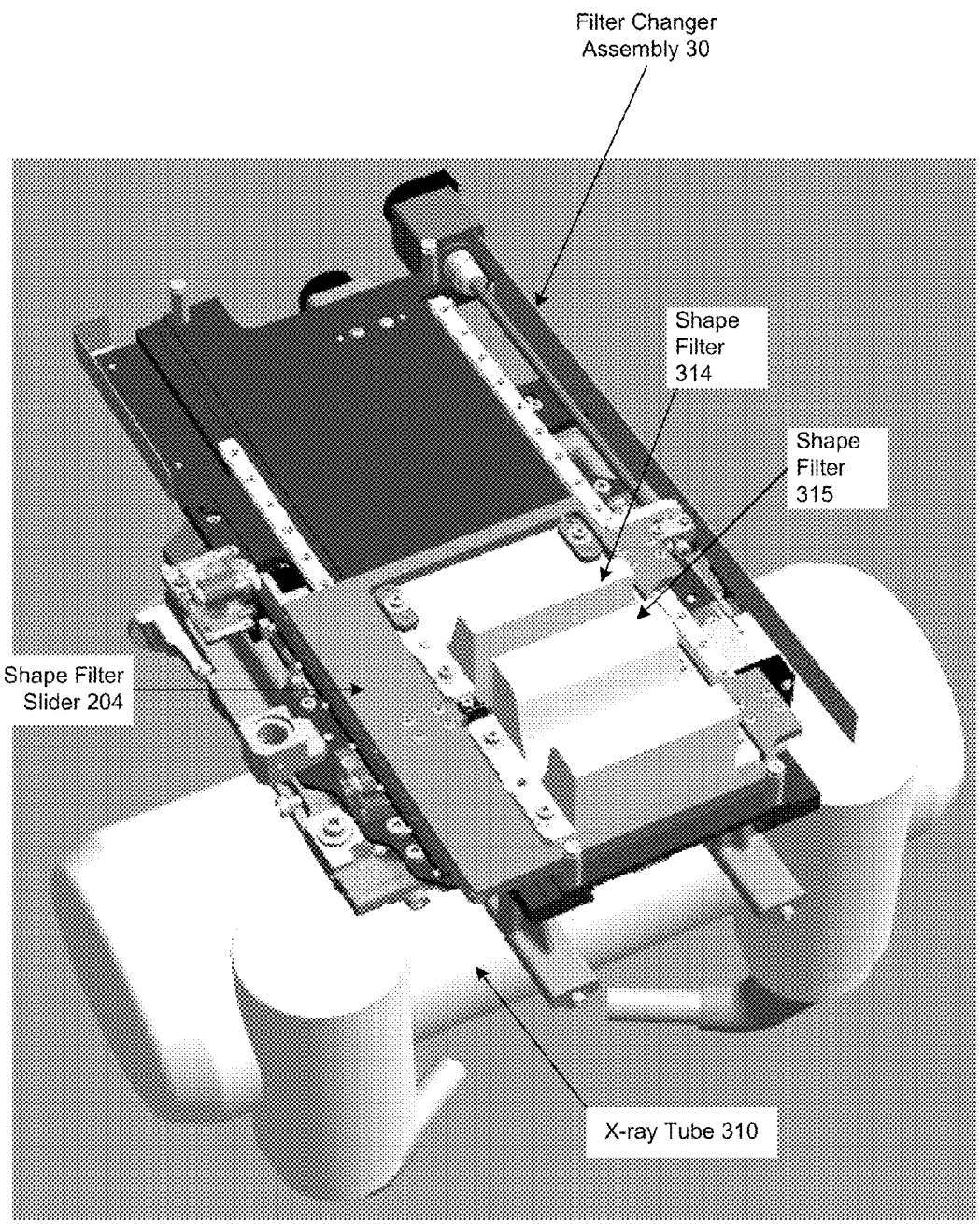

FIGS. 3 and 4 illustrate an embodiment of a filter changing assembly 30 and an x-ray tube 310 according to the invention. In the example of FIG. 3, a beam hardening filter 203 is situated over the beam exit, while the shape filters 314 and 315 are in their storage positions. In the example of FIG. 4, the shape filter slider 204 has been moved (as described above) so that the shape filter 314 is aligned over the beam hardening filter 203 (not visible in FIG. 4).

In FIGS. 3 and 4, the filter changing assembly 30 is mounted transverse to the longitudinal axis of the x-ray tube 310; however, the invention is not so limited. In general, depending on how they are mounted, the filter sliders 202 and 204 can move in the axial or radial direction with respect to the orientation of the x-ray tube 310.

The x-ray tube 310 can contain a pre-collimator that prevents the storage position from being exposed to radiation. Also, a blade (jaw) assembly, which contains some number of motorized and position-controlled blades (e.g., four blades), can be located between the x-ray tube 310 and the filter changer assembly 30. The blade assembly is used to narrow the beam so that no elements external to the active surface of the detector 40 (FIG. 1) are irradiated.

Figure 5:
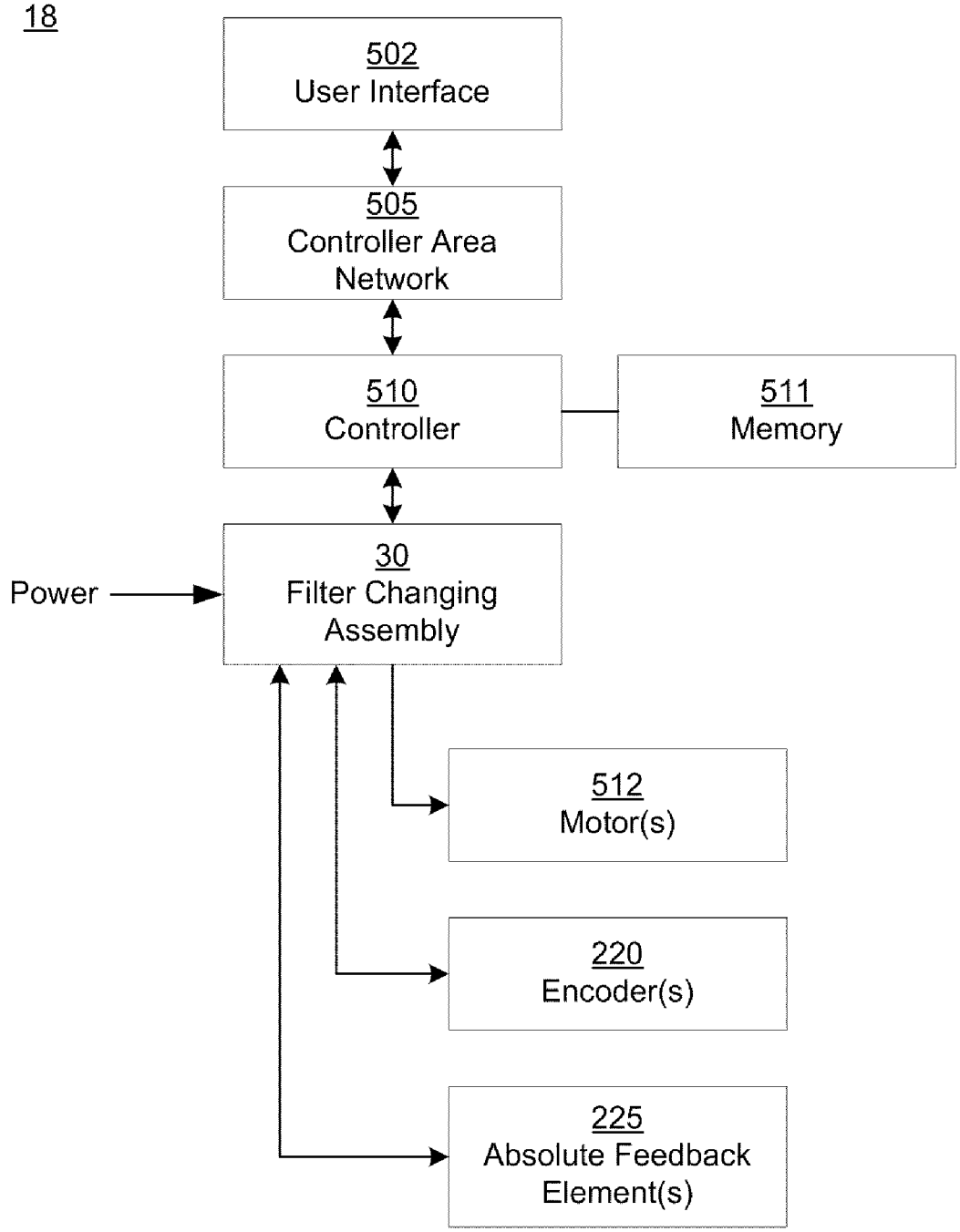
FIG. 5 illustrates elements of an embodiment of a control system according to the invention.

FIG. 5 illustrates elements of an embodiment of a control system 18 according to the invention. In the example of FIG. 5, the control system 18 includes a controller 510 that is coupled to (in communication with) the controller area network (CAN) 505. However, embodiments according to the present invention are not limited to the CAN standard and protocol. The controller 510 can also be coupled to or include a memory 511.

In one embodiment, a user interface 502 (e.g., a control console or the like) is coupled to the control system 18. With reference to FIG. 1, an operator at the user interface 512 can input commands to control operation of the filter changing assembly 30. Significantly, the user interface 512, and hence the operator, can be in a room other than the treatment room and still control the filter changing assembly 30. More specifically, as described above, an operator can remotely and automatically change, insert, and remove filters.

The control system 18 can include one or more motors 512, one or more encoders 220, and one or more absolute feedback elements 225. A single motor and one feedback element may be sufficient, but one encoder 220 and one absolute feedback element 225 provide diverse redundancy and may be required by government regulations.

As presented above, the encoder 220 is used to detect, measure, and monitor filter positions. The absolute feedback element 225 provides a diverse and redundant channel to the encoder 220 for position detection, and can be used to establish the initial position of the filter when the encoder is not yet initialized.

More specifically, the encoder 220 provides positions based on differences (e.g., distance traveled). Thus, the evaluating electronics (e.g., counters) have to be set to an initial value at a well-defined absolute position. The shape filter slider 202 (FIG. 2) uses physical (mechanical) end stops as the well-defined absolute positions. The control system 18 uses values from the absolute feedback element 225 to locate the end stops in an accurate and reproducible way.

Once the encoder 220 is initialized, it can serve as the primary (accurate) position read-out. During normal operation (once initialized), the controller 510 checks both the encoder 220 and the absolute feedback element 225 for plausibility. If they do not agree, then a possible mechanical problem has occurred, and the control system 18 goes into a safe state (e.g., it stops and notifies the operator).

Figure 6:
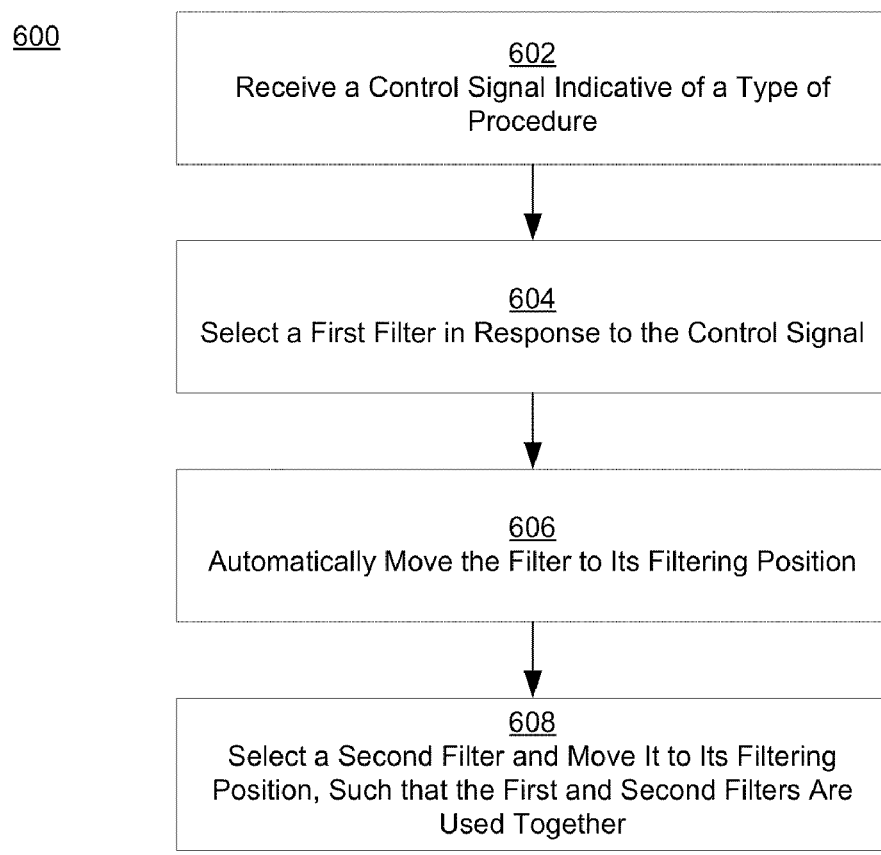
FIG. 6 is a flowchart of an embodiment of a computer-implemented method of operating a radiology system according to the invention.

FIG. 6 is a flowchart 600 of a method of operating a radiology system (e.g., the system 100 of FIG. 1) according to an embodiment of the invention. Although specific steps are disclosed in the flowchart 600, such steps are exemplary. That is, the present invention is well-suited to performing various other steps or variations of the steps recited in the flowchart 600. In one embodiment, the method of the flowchart 600 is performed by, for example, the control system 18 of FIG. 5.

In block 602 of FIG. 6, a control signal that identifies a type of radiation procedure (e.g., a scan, imaging, or treatment procedure) to be performed is received. Alternatively, the control signal can identify the filter or filters that are to be used to perform a particular type of radiation procedure. In general, as discussed above, filters can be selected and inserted depending on a selected type of scan, imaging, or treatment procedure.

In block 604, once the control signal is received, then the control system 18 (FIG. 5) automatically selects a first filter (e.g., a beam hardening filter or a shape filter) that was defined in advance for the specified procedure. In one embodiment, the control signal is produced in response to a user-generated command that is input from a location outside a room (e.g., the treatment room) that houses the radiology system 100 (FIG. 1).

In block 606 of FIG. 6, the control system 18 (FIG. 5) causes the selected filter to be moved into a precise filtering position that was also defined in advance for the specified procedure. The filter can be moved, and the filter position can be fine-tuned, remotely from outside the treatment room and during radiation exposure.

In block 608 of FIG. 6, once the control signal is received, then the control system 18 (FIG. 5) automatically selects a second filter (e.g., a beam hardening filter or a shape filter) that was also defined in advance for the specified procedure, and causes the second selected filter to be moved into a precise filtering position that was also defined in advance for the specified procedure, such that the first and second filters can be used together to filter an incident radiation beam. The second filter can also be moved and its position fine-tuned remotely from outside the treatment room and during radiation exposure.

In summary, embodiments according to the present invention provide a filter changing assembly that allows multiple filters to be automatically selected and moved into a filtering position inside the path of a radiation beam. Accordingly, it is not necessary for an operator to enter the treatment room to change filters or filter positions. Consequently, the process of setting up filters, including alignment and calibration, is significantly reduced.

Embodiments according to the invention may also be used in combinations that include both moveable and fixed-position filters. For example, the disclosed filter changing assembly can be used in combination with a fixed-position flattening filter (used to flatten the dose of an x-ray beam, for example). Types of filters other than shape filters and beam hardening filters can be used in place of or in addition to those types of filters.

The foregoing descriptions of specific embodiments of the present invention have been presented for purposes of illustration and description. They are not intended to be exhaustive or to limit the invention to the precise forms disclosed, and many modifications and variations are possible in light of the above teaching. The embodiments described herein were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

What is claimed is:

1. A filter changing assembly comprising:
a plurality of radiation filters comprising:
   a plurality of shape filters operable for shaping a radiation beam; and
   a plurality of beam hardening filters operable for affecting the energy spectrum of said radiation beam; and
a control system coupled to said plurality of radiation filters and operable for selecting a first filter from said plurality of radiation filters and for automatically moving said first filter from one position to another position, wherein said control system is also operable for selecting a second filter from said plurality of radiation filters and for automatically moving said first and second filters such that said first and second filters are used together to filter said radiation beam, wherein said first filter is one of said shape filters and said second filter is one of said beam hardening filters.

2. The assembly of claim 1 further comprising:
a motor operable for moving said radiation filters; and
a position detector operable for monitoring positions of said radiation filters.

3. The assembly of claim 1 further comprising a guide upon which said radiation filters slide back-and-forth.

4. The assembly of claim 1 further comprising a carousel upon which said radiation filters are rotated in and out of position.

5. A radiology system comprising:
a surface for supporting a subject;
a radiation source coupled to a gantry, wherein said gantry is moveable about said surface and wherein said radiation source is operable for projecting a beam of radiation toward said subject;
a detector operable for sensing radiation that passes through said subject; and
a filter changing assembly coupled to said gantry and comprising a plurality of filters, wherein said filter changing assembly is operable for selecting a first filter from said plurality of filters and for automatically moving said first filter into and out of a position for filtering said beam between said radiation source and said subject, wherein further said filter changing assembly is operable for selecting a second filter from said plurality of filters and for automatically moving said second filter into and out of a position for filtering said beam between said radiation source and said subject, wherein said first filter is a shape filter for shaping said beam and said second filter is a beam hardening filter for affecting the energy spectrum of said beam, and wherein said first and second filters are used together to filter said beam.

6. The system of claim 5 further comprising a control system operable for selecting said first filter and said second filter in response to a control signal, wherein said control signal is produced in response to a user-generated command that is input from a location outside a room that houses said radiology system.

7. The system of claim 5 further comprising a control system operable for positioning said first filter and said second signal in response to a control signal, wherein said control signal is produced in response to a user-generated command that is input from a location outside a room that houses said radiology system.

8. The system of claim 5 wherein said filters move in the axial direction relative to the orientation of said radiation source.

9. The system of claim 5 wherein said filters move in the radial direction relative to the orientation of said radiation source.

10. The system of claim 5 further comprising:
a motor operable for moving said filters; and
a position detector operable for monitoring positions of said filters.

11. The system of claim 5 wherein said radiation source comprises an x-ray tube and wherein said system comprises a cone beam computed tomography system.

12. A method of operating a radiology system, said method comprising:
receiving a control signal indicative of a type of radiation procedure;
in response to said control signal, selecting a first filter from a plurality of filters, wherein said plurality of filters comprises a first plurality of shape filters operable for shaping a radiation beam and a second plurality of beam hardening filters operable for changing the energy spectrum of said radiation beam;
automatically causing said first filter to move from its respective storage position to its respective filtering position or an intermediate position;
selecting a second filter from said plurality of filters; and
automatically causing said second filter to move from its respective storage position to its respective filtering position, wherein said first filter is one of said shape filters and said second filter is one of said beam hardening filters, and wherein said first and second filters are used together to filter said radiation beam.

13. The method of claim 12 wherein said control signal is produced in response to a user-generated command that is input from a location outside a room that houses said radiology system.

14. The method of claim 12 further comprising:
identifying said type of procedure; and
automatically selecting said first filter and said second filter and their respective filtering positions according to said type of procedure.

15. The method of claim 12 wherein said shape filters are moveable back-and-forth between i) a first filtering position that is between a radiation source and a target and ii) a first storage position that is outside of said radiation beam's path, and wherein said beam hardening filters are moveable back-and-forth between i) a second filtering position that is between said radiation source and said target and ii) a second storage position that is outside of said radiation beam's path.

* * * * *